United States Patent
Stamnes et al.

(10) Patent No.: US 7,822,468 B2
(45) Date of Patent: Oct. 26, 2010

(54) METHOD AND AN ARRANGEMENT FOR THE DETERMINATION OF THE OPTICAL PROPERTIES OF A MULTI-LAYERED TISSUE

(75) Inventors: Jakob J. Stamnes, Oslo (NO); Knut Stamnes, Maplewood, NJ (US)

(73) Assignee: Balter, AS, Bergen (NO)

( * ) Notice: Subject to any disclaimer, the term of this patent is extended or adjusted under 35 U.S.C. 154(b) by 907 days.

(21) Appl. No.: 10/471,111

(22) PCT Filed: Mar. 6, 2002

(86) PCT No.: PCT/NO02/00095
§ 371 (c)(1),
(2), (4) Date: Oct. 23, 2003

(87) PCT Pub. No.: WO02/069792
PCT Pub. Date: Sep. 12, 2002

(65) Prior Publication Data
US 2004/0092824 A1  May 13, 2004

(30) Foreign Application Priority Data
Mar. 6, 2001 (NO) .................................. 20011131

(51) Int. Cl.
*A61B 5/00* (2006.01)
(52) U.S. Cl. ........................................ 600/476; 600/473
(58) Field of Classification Search .................. 600/310, 600/473, 476
See application file for complete search history.

(56) References Cited

U.S. PATENT DOCUMENTS

| 5,813,988 | A * | 9/1998 | Alfano et al. ............... 600/476 |
|---|---|---|---|
| 6,208,749 | B1 | 3/2001 | Gutkowicz et al. |
| 6,307,957 | B1 | 10/2001 | Gutkowicz et al. |
| 6,324,417 | B1 | 11/2001 | Cotton |
| 2001/0032053 | A1 * | 10/2001 | Hielscher et al. ............... 702/22 |

FOREIGN PATENT DOCUMENTS

WO  WO00/37924  * 6/2000

OTHER PUBLICATIONS

Siegel, A.M., J.J.A. Marota, and D.A. Boas. "Design and evaluation of a continuous-wave diffuse optical tomography system". 1999. Optics Express. vol. 4, No. 8, pp. 287-298.*
Rolston et al. "A Well Collimated Quasi-Continuous Atom Laser". Mar. 4, 2000. http://web.archive.org/web/20000304120946/http://physics.nist.gov/Divisions/Div842/Gp4/AtomOptics/intro.html.*

* cited by examiner

*Primary Examiner*—Brian Casler
*Assistant Examiner*—Peter Luong
(74) *Attorney, Agent, or Firm*—Mark S. Leonardo; Brown Rudnick LLP

(57) ABSTRACT

The present invention relates to a method and an arrangement for the determination of the optical properties of a multi-layered tissue. More specifically, the invention relates to a method for the detection and characterisation of tumors in a tissue.

15 Claims, 3 Drawing Sheets

Figure 1:
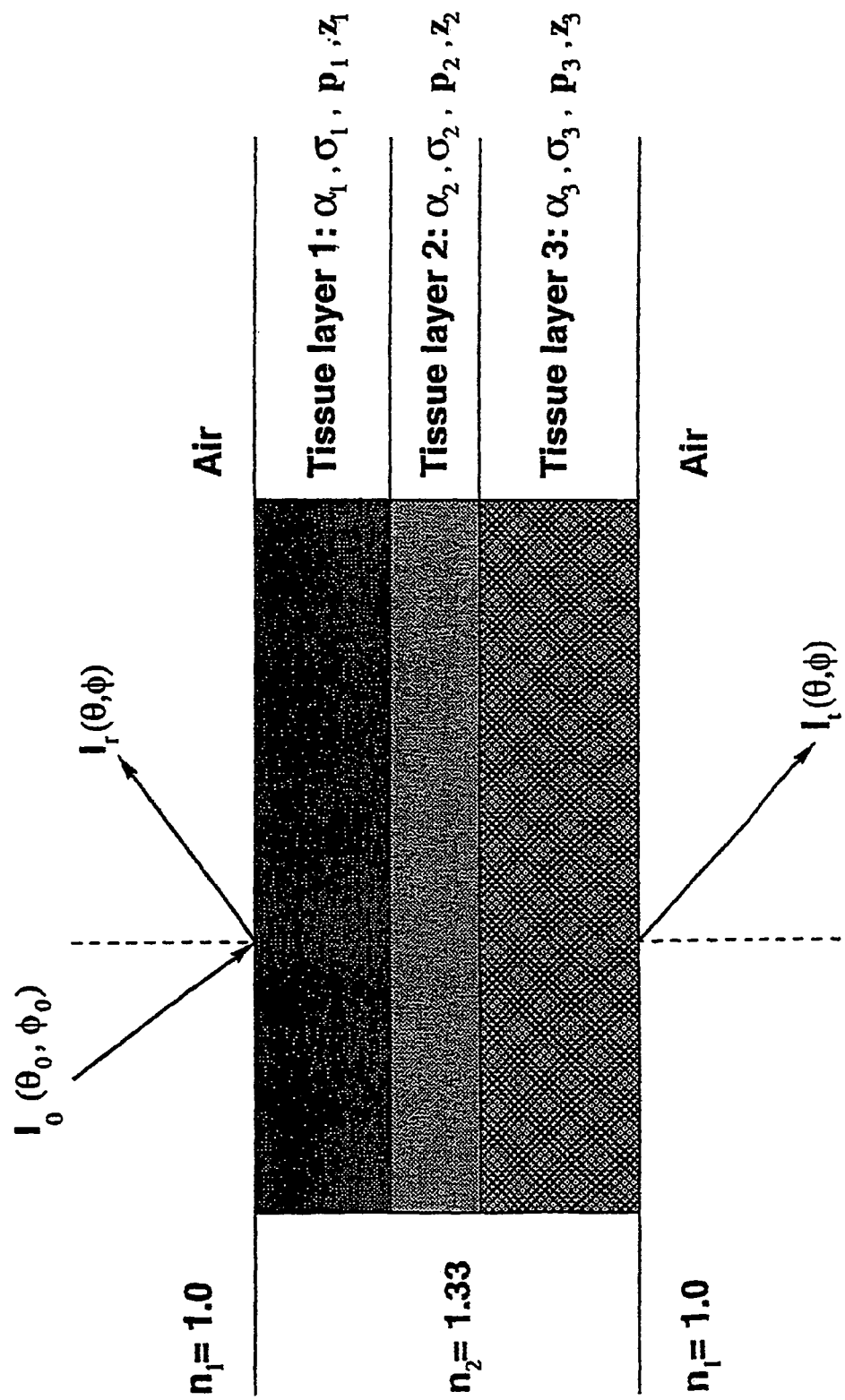

METHOD AND AN ARRANGEMENT FOR THE DETERMINATION OF THE OPTICAL PROPERTIES OF A MULTI-LAYERED TISSUE

BACKGROUND OF THE INVENTION

1. Field of the Invention

The present invention relates to a method and an arrangement for the determination of the optical properties of a multi-layered tissue. More specifically, the invention relates to a method for the detection and characterization of tumors in a tissue.

2. Description of Related Art Including Information Disclosed Under 37 CFR 1.97 and 1.98

New developments in imaging by means of visible and near-infrared light show promise in medical diagnosis, because light can offer three key benefits over traditional diagnostic tools based on e.g. X-rays, ultrasound, or nuclear magnetic resonance. First, light at different wavelengths interacts with tissue in distinctive ways and forms the basis for spectroscopy, which allows one to optimize the wavelength for a specific application. Second, image-processing methods are becoming powerful enough to make it possible to use just a few photons, and thus allow imaging based on low-level or noisy signals. Third, light offers a good compromise between the lower-resolution radio frequency or ultrasound imaging and the shorter wavelength, higher resolution, but harmful ionizing radiation of X-rays. Also, optical methods are usually non-invasive and non-toxic, and have the potential to be realized in terms of compact and inexpensive devices.

Any imaging or spectroscopic method must deal with both the absorption by the primary component of tissue, i.e. the aquatic solution, and the absorption and scattering by various types of tissue "particles". Spectroscopy is used for measuring time-dependent total variations in the absorption and scattering in large volumes of tissue. For example, brain oximetry (haemoglobin spectroscopy) can reveal internal bleeding caused by head injury. Imaging is important when it is of interest to detect a localized heterogeneity of the tissue, such as an early breast or brain tumor or a small amount of bleeding in the brain. Then imaging enables one to identify the site of the trauma and differentiate it from the surrounding tissue. Tumors represent a structural anomaly that one desires to detect, localize, and classify. Tumor growth is associated with (i) a larger blood volume resulting from a relatively larger number density and volume fraction of blood vessels in the tumor, (ii) increased concentrations of the intracellular organelles required for the energy production associated with rapid growth, and (iii) accumulation of highly scattering calcium precipitates. Some of these properties are expected to be helpful in classifying tumors as benign, malignant, and so on.

Light that enters tissue is absorbed and scattered by compounds in the tissue called chromophores. The major chromophores are melanin, haemoglobin, and cytochromes. Melanin is a pigment that colors our skin and protects us from sunburn. It attenuates UV light strongly by acting as a Rayleigh scatterer. Hemoglobin (Hb) is a colored pigment found in red blood cells. It is a large molecule that can bind oxygen molecules to form $HbO_2$. Cytochromes consist of a series of enzymes found in the membrane of the mitochondria. They have absorption spectra that depend on whether the enzyme is in its oxidized or reduced state. Cytochromes can be monitored by optical means. For example, NADH is an important compound that absorbs strongly in the UV (310-375 nm). If NADH is exposed to UV light, it will fluoresce with a broad-band emission spectrum around 460 nm. The absorption spectrum of Hb is different from that of $HbO_2$. Thus, highly oxygenated arterial blood looks bright red, while venous blood containing more deoxygenated haemoglobin appears bluish red. The absorption coefficient varies with wavelength, but is typically 0.02-0.1 per millimeter in the visible and NIR parts of the spectrum. It also depends on chromophore content (especially the amount of blood). By tissue particle is meant a small volume of tissue with a complex refractive index that is different from that of the surrounding medium. The absorption by the aquatic component is known or can be measured for healthy tissue. A small volume surrounding a tumor is characterized by increased blood concentration and thus enhanced or anomalous absorption. Particles much smaller than the wavelength of light consisting of cell nuclei or mitochondria are called Rayleigh scatterers. Particles much larger than the wavelength of light consisting of cells or groups of cells are called Mie scatterers. The scattering coefficient varies with wavelength but is typically in the range 20-100 per millimeter.

Knowledge of the optical properties of biological tissue is the critical basis for carrying out studies in biomedical imaging as well as for developing instruments for medical diagnosis.

The physiological state of a biological tissue can be obtained from its absorption and scattering coefficients. By physiological state is meant the relative concentrations of aquatic and non-aquatic components as well as the chemical composition of non-aquatic tissue components including blood vessels, organelles, etc. Thus, it is desirable to develop accurate and reliable methods for determining optical properties of tissue.

Optical coherence tomography (OCT) has been successfully applied in biomedical imaging. This method relies on the use of coherent light, and it can be used to image the architectural morphology or glandular organization of tissues. However, its penetration depth is limited to 2-3 mm, and this technique, as currently practiced, does not provide the information needed to determine the optical properties of a biological system.

Since coherent light provides limited depth information, many current optical imaging techniques rely on the use of diffuse light, which carries information about deeper layers, i.e. about 4-8 mm within the tissue.

These methods include;
(i) time-resolved techniques for detection of so-called "snake" or "ballistic" photons that have propagated along nearly-straight paths
(ii) diffuse optical tomography, and
(iii) tomographic imaging using diffuse photon density waves created by intensity-modulating the incident light energy.

In imaging with diffuse light, approaches to the solution of the radiative transfer problem are frequently based on the diffusion approximation to the radiative transfer equation.

By the term "radiative transfer problem" is meant transport of light in a multiple scattering medium such as tissue.

A review of the current literature is given in table 1.

| Method | Physical Principle | Strength | Limitation | Equipment Need | Commercial Feasibility | Comments |
|---|---|---|---|---|---|---|
| OCT | based on coherent light | high spatial resolution | penetration depth is limited | optical gating & correlation devices | available | performs architectural morphology, but is unable to image tissue optical properties |
| Laser CT (1) | based on CT theory | can determine extinction coefficient | penetration depth is limited | heterodyne detection device | under investigation | based on transmitted signal, can only be applied to a very thin layer of tissue |
| Time-resolved diffuse imaging | based on ballistic photons | can determine optical properties | penetration depth is limited | high time-resolution device | promising | high time resolution is necessary, but is difficult to do |
| CW diffuse optical tomography (2) | based on diffuse photons | real-time functional imaging | signal to noise problem | CW laser sources | under investigation | performs quantitative functional brain imaging, but does not determine tissue optical properties |
| TOAST (3) | based on finite element model | real-time functional imaging | based on time-resolved measurements | pulsed laser & high time-resolution device | under investigation | contains the limitation inherent in time-resolved techniques |
| Diffuse optical reflection tomography (4) | based on diffusion theory | simple & fast | determines only absorption coefficient | CW laser source | under investigation | it is insufficient to use only absorption coefficient to describe a biological tissue |
| DPDW tomography (5) | based on diffuse photon density waves | analytical solution for DPDW | transmitted DPDW signal is weak | light source modulation | under investigation | cannot determine optical properties of the background tissue |
| Phased array imager (6) | based on diffuse photon density waves | fast Imaging of brain function | resolution is questionable | CW light source & modulation | under investigation | additional work needed to retrieve optical properties from measured signal |
| Frequency-domain optical tomography (7) | based on diffusion theory | determine optical properties | resolution & accuracy is questionable | diode laser and intensity modulator | under investigation | cannot retrieve scattering coefficient properly; unable to determine optical properties of the background |

(1) Watanabe et al. (1998). (2) Siegel et al. (1999). (3) Schweiger et al. (4) Cheng and Boas (1998). (5) Boas et al. (1997). Chen et al. (1998). Li et al. (2000). (6) Chance et al. (1998). (7) Pogue et al. (1997).
CT: Computed Tomography
TOAST: Time-resolved Optical Absorption and Scatter Tomography
DPDW: Diffuse Photon Density Wave 1. Even though time-resolved techniques offer the potential for determining the optical properties of tissues, their reliance on high time-resolution measurements makes it a very challenging task to carry out experimental studies for validating the methodology, and to develop suitable bedside instrumentation.
2. Quite a few of the available techniques have been used only to study the differences between the absorption coefficients of the object and its surrounding medium (e.g. Cheng, x. and D. A. Boas, 1998: Diffuse optical reflection tomography with continuous-wave illumination. Opt. Express 3, No. 3, 118-123). It is insufficient to use solely the absorption coefficient to describe a biological tissue or an object embedded in such a tissue, since scattering can usually not be ignored in such a medium.
3. Most of the available tomographic optical imaging methods are focused on studying the optical properties (the absorption and scattering coefficients and the asymmetry factor or phase function) of an object that is embedded in a turbid medium, e.g. a tumor in healthy tissue, assuming that the optical properties of the background medium (healthy tissue) are known. These techniques cannot easily be used to study the optical properties of the turbid background medium (healthy tissue). However, accurate knowledge of the optical properties of the background medium is critical for success in biomedical imaging.

The above-described limitations of existing approaches clearly show that there is an urgent need to develop and provide reliable methods to determine both;
(1) the optical properties of healthy biological tissue, and
(2) the location and optical properties of an object (such as a tumor) that is embedded in the healthy tissue.

BRIEF SUMMARY OF THE INVENTION

The overall objective of the present invention is thus to provide a new method for determining the optical properties of a multi-layered tissue. In this context the term "optical properties" includes the determination of the absorption and scattering coefficients, and also the asymmetry factor. By the term "multi-layered tissue" is meant a tissue with a stratified structure such that the optical properties may vary from one layer to the next.

A further object of the present invention is to use this method for the diagnosis and localization of tumors embedded in such a layered tissue.

Our approach is based on rigorous radiative transfer theory (described in more detail below). A sophisticated state-of-the-art radiative transfer model for the coupled air/tissue system is used to provide both forward and inverse algorithms for characterizing the optical properties of such a multi-layered tissue.

Further, the algorithms are used to provide a method to determine the location and optical properties of an object (such as a tumor) that may be embedded in such a layered tissue.

Also provided is an experimental arrangement (FIG. 3), and validation studies will be carried out.

The theoretical foundation for the method and arrangement in accordance with the present invention is detailed below, and investigations in progress are as follows:

(1) Forward simulations in which a multi-layered tissue is illuminated by a collimated electromagnetic beam, successively from several directions. For each illumination direction a comprehensive radiative transfer model for the coupled air/tissue system will be used to solve for the reflected diffuse light at several viewing angles.
(2) Development of a method for retrieving the optical properties and layer thickness of each of the top two layers of a multi-layered tissue based on reflected radiances obtained from forward simulations.
(3) Design of an experimental set-up for testing and validating the theoretical simulations described in (1) and (2) above.
(4) Development of an algorithm to determine the location and optical properties of an object that is embedded in a layered tissue based on the results obtained in the studies described above.

Optical diagnostics can be classified as either imaging or spectroscopy, or a combination of both. Optical coherence tomography (OCT), as a high-resolution, shallow imaging tool, has been developed in several research groups around the world (Huang, D., E. A. Swanson, C. P. Lin, J. S. Schuman, W. G. Stinson, W. Chang, M. R. Hee, T. Flotte, K. Gregory, C. A. Puliafato, and J. G. Fujimoto, 1991: Optical coherence tomography. Science 254, 1178-1181.; Izatt, J. A., M. Kulkarni, K. Kobayashi, M. V. Sivak, J. K. Barton, and A. J. Welsh, 1997: Optical coherence tomography for biodiagnostics. Optics & Photonics News 8, 41-47; Schmitt, J. M., 1998: OCT elastography: imaging microscopic deformation and strain of tissue. Opt. Express3, No. 6, 199-211). OCT can be used to perform high-resolution, cross-sectional tomographic imaging of the internal microstructure in materials and biological systems by measuring echo time delays and magnitudes of backscattered light (Huang et al., 1991; Fujimoto et al., 2000). With continuous wave illumination a transverse resolution of 10 μm can be obtained with OCT, but the penetration depth is limited to 2-3 millimeters at most (Carts-Powell, Y., 1999: Optical tools offer minimally invasive medical diagnostics. Optics & Phonotics News 10, No. 6, 33-37; Fujimoto, J. G., W. Drexler, U. Morgner, F. Kartner, and E. Ippen, 2000: Optical coherence tomography using echoes of light. Optics & Photonics News 11, No. 1, 24-31).

OCT can be used to image the architectural morphology or glandular organization of tissues, but it cannot be used to determine the optical properties of a biological system. On the other hand, OCT measurements of ultra-fast echo time delays require optical gating and correlation techniques, since direct electronic detection is not possible.

Coherent imaging is useful, but most of the light that enters the tissue is either absorbed or scattered several times. Much ongoing research, e.g., Boas, D. A., M. A. O'Leary, B. Chance, and A. G. Yodh, 1997: Detection and characterization of optical inhomogeneities with diffuse photon density waves: a signal-to-noise analysis. Appl. Opt. 36, 75-92; Chance, B., E. Anday, S. Nikoa, S. Zhou, L. Hong, K. Worden, C. Li, T. Murray, Y. Ovetsky, D. Pidikiti, and R. Thomas, 1998: A novel method for fast imaging of brain function, non-invasively, with light. Opt. Express 2, No. 10, 411-423; Chen, B., J. J. Stamnes, and K. Stamnes, 1998: Reconstruction algorithm for diffraction tomography of diffuse photon density waves in a random medium. Pure Appl. Opt. 7, 1161-1180; Cheng, x. and D. A. Boas, 1998: Diffuse optical reflection tomography with continuous-wave illumination. Opt. Express 3, No. 3, 118-123; Durduran, T., J. P. Culver, M. J. Holboke, X. D. Li, L. Zubkov, B. Chance, D. N. Pattanayak, and A. G. Yodh, 1999: Algorithms for 3D localization and imaging using near-field diffraction tomography with diffuse light. Opt. Express 4, No. 8, 247262; Jacques, S. L., I. S. Saidi, A. Ladner, D. G. Oelberg, 1997: Developing an optical fiber reflectance spectrometer to monitor bilirubinemia in neonates. SPIE Proceedings of Laser-Tissue Interaction VIII, edited by S. L. Jacques, 2975, 115-124; Kienle, A., M. S. Patterson, N. Dognitz, R. Bays, G. Wagnieres, and H. van den Bergh, 1998: Noninvasive determination of the optical properties of two-layeres turbid media. Appl. Opt. 37, 779-791; Klose, A. D. and A. H. Hielscher, 1999: Iterative reconstruction shceme for optical tomography based on the equation of radiative transfer. Medical Phys. 26, 1698-1707; Patterson, M. S. B. Chance, and B. C. Wilson, 1989: Time resolved reflectance and transmittance for noninvasive measurement of tissue optical properties. Appl. Opt. 28, 2331-2336; Siegel, A. M., J. J. A. Marota, and D. A. Boas, 1999: Design and evaluation of a continuous-wave diffuse optical tomography system. Opt. Express 4, No. 8, 287-298; Wang, R. K. and Y. A. Wickramasinghe, 1998. Fast algorithm to determine optical properties of a turbid medium from time-resolved measurements. Appl. Opt. 37, 7342-7351, Yodh, A. and B. Chance, 1995, Spectroscopy and imaging with diffusing light. Physics Today 3, 34-40) is aimed at developing methods for interpreting diffuse images. One approach is based on a time-resolved technique to measure the diffuse photons from pulsed light sources that have propagated along nearly straight paths ("ballistic" photons) (Wang and Wickramasinghe, 1998). Techniques that rely on time-resolved measurements provide the opportunity, at least in principle, to determine the optical properties of tissue (Patterson, M. S. B. Chance, and B. C. Wilson, 1989: Time resolved reflectance and transmittance for noninvasive measurement of tissue optical properties. Appl. Opt. 28, 2331-2336; Wang, R. K. and Y. A. Wickramasinghe, 1998. Fast algorithm to determine optical properties of a turbid medium from time-resolved measurements. Appl. Opt. 37, 7342-7351).

In practice, however, it is very difficult to perform such measurements, not only because scattering rapidly reduces the number of "ballistic" photons along the path, but also because an extremely high time resolution is necessary.

Research on diffuse optical tomography has relied on several approaches. Siegel et al. (Siegel, A. M., J. J. A. Marota, and D. A. Boas, 1999: Design and evaluation of a continuous-wave diffuse optical tomography system. Opt. Express 4, No. 8, 287-29) built a portable continuous-wave diffuse optical tomography system consisting of 18 laser diode sources (9 at 780 nm and 9 at 830 nm) and 16 silicon detectors, but they did not use their method and results to obtain the optical properties of the biological tissue. The time-resolved optical absorption and scattering tomography technique developed by the group at the University College London (Schweiger, M., L. Zhukov, S. R. Arridge, and C. Johnson, 1999: Optical tomography using the SCIRun problem solving environment: Preliminary results for three-dimensional geometries and parallel processing. Opt. Express 4, No. 8, 263-269) relies on a finite element forward model to simulate light transport in scattering media in order to reconstruct the internal distribution of optical parameters from time-of-flight data. Since this technique is based on time-resolved measurements it suffers from the same limitations as the methods discussed above. Another example is the diffuse optical reflection tomography developed by Cheng and Boas (1998), which can be used to determine the absorption coefficient of an object embedded in a turbid medium. Note that, in general, it is insufficient to use only the absorption coefficient to describe a turbid medium such as a biological tissue or an object embedded in such a turbid medium.

Diffuse photon density waves have been used for tomographic imaging of objects embedded in a turbid medium (Boas, D. A., M. A. O'Leary, B. Chance, and A. G. Yodh, 1997: Detection and characterization of optical inhomogeneities with diffuse photon density waves: a signal-to-noise analysis. Appl. Opt. 36, 75-92; Chen, B., J. J. Stamnes, and K. Stamnes, 1998: Reconstruction algorithm for diffraction tomography of diffuse photon density waves in a random medium. Pure Appl. Opt. 7, 1161-1180; Li, X., D. N. Pattanayak, T. Durduran, J. P. Culver, B. Chance, and A. G. Yodh, 2000: Nearfield diffraction tomography with diffuse photon density waves. Phys. Rev. E 61, 4295-4309). The advantage of using diffuse photon density waves is that such a wave has a well-defined phase front. Measurements of both the phase and the amplitude of the transmitted diffuse photon density wave can be used to study objects that are embedded in a turbid background medium with known optical properties (Scattering and absorption coefficients). Since the signal of the transmitted diffuse photon density wave is usually very weak, this technique cannot be applied to a thick turbid medium. Also, tomographic imaging using diffuse photon density waves cannot be employed for determining the optical properties of the turbid background medium. Another approach relies on the use of diffuse photon density waves in conjunction with reflectance measurements of light from layered media to determine the structure of light from layered media to determine the structure of a layered tissue (Svaasand, L. O., T. Spott, J. B. Fishkin, T. Pham, B. J. Tromberg, and M. W. Berns, 1999: Reflectance measurements of layered media with diffuse photon-density-waves: a potential tool for evaluating deep burns and subcutaneous lesions. Phys. Med. Biol. 44, 801-813). Since the wavelength of the diffuse photon density wave is usually large, say at least a few centimeters, measurements of the phase of the diffuse photon density wave can only provide low-resolution information about the internal structure of the tissue.

Fluorescence spectroscopy constitutes an established way of applying medical diagnostics (e.g., Chance, B., 1996: Use of intrinsic fluorescence signals for characterizing tissue metabolic states in health and disease. SPIE Proc. 2679, 2-7; Gardner, C. M., S. L. Jacques, and A. J. Welch, 1996: Fluorescence spectroscopy of tissue: recovery of intrinsic fluorescence from measured fluorescence. Lasers surg. Med. 18, 129-138), either to the tissue itself or to some agent such as a dye used in photodynamic therapy. By analyzing the "colors" of the emitted light following optical excitation of a tissue sample, one may determine if the tissue is normal, benign, or cancerous. The underlying physical basis for other spectroscopic techniques such as Raman scattering, phosphorescence, and elastic scattering, is that the light-tissue interaction is strongly influenced by the chemical composition and the cellular structure of the tissue. These methods require that either optical biopsies are performed, or that healthy tissues is are cut out or exposed to harmful ionizing radiation (Carts-Powell, Y., 1999: Optical tools offer minimally invasive medical diagnostics. Optics & Phonotics News 10, No. 6, 33-37).

Since many parts of the body such as skin, esophagus, stomach, intestine, bladder, and head have a layered tissue structure, it is increasingly recognized that for biomedical imaging a layered tissue model is more realistic than a homogeneous model. Several researchers have investigated the solution of the diffusion equation for layered turbid media. Takatani and Graham (Takatani, S. and M. D. Graham, 1979: Theoretical analysis of diffuse reflectance from a two-layer tissue model. IEEE Trans. Biomed. Eng. BME-26, 656-664) and Schmitt et al. (Schmitt, J. M. G. X. Zhou, E. C. Walker, and R. T. Wall, 1990: Multilayer model of photon diffusion in skin. J. Opt. Soc. Am. A 7, 2141-2153) derived analytical formulas for the steady-state reflectance by use of Green's functions to solve the diffusion equation, while Dayan et al. (Dayan, I., S. Havlin, and G. H. Weiss, 1992: Photon migration in a two-layer turbid medium, A diffusion analysis. J. Mod. Opt. 39, 1567-1582) applied Fourier and Laplace transforms to obtain expressions for the steady-state and time-resolved reflectance. Keijzer et al. (Keijzer, M., W. M. Star, and P. R. M. Storchi, 1988: optical diffusion in layered media. Appl. Opt. 27. 1820-1824) and Schweiger et al. (Schweiger, M., S. R. Arridge, M. Hiraoka, and D. T. Deply, 1995: The finite element model for the propagation of light in scattering media: Boundary and source conditions. Med. Phys. 22, 1779-1792) employed a finite element method, and Cui and Ostrander (Cui, W. and L. E. Ostrander, 1992: The relationship of surface reflectance measurements to optical properties of layered biological media. IEEE Trans. Biomed. Eng. 39, 194-201) used a finite difference approach.

However, these researchers did not compare their results to solutions of the transport equation, and the feasibility of deriving the optical properties of the two layers adopted in their models has not been studied. Kienle et al. (Kienle, A., M. S. Patterson, N. Dognitz, R. Bays, G. Wagnieres, and H. van den Bergh, 1998: Noninvasive determination of the optical properties of two-layeres turbid media. Appl. Opt. 37, 779-791) solved the diffusion equation using a Fourier transform approach for a two-layer turbid medium having a semi-infinite second layer. It is of interest to note the following statement of these authors:

"although the solutions of the diffusion equation for the reflectance from a two-layered medium are quite close to the results of the transport theory, the errors in determining the optical properties caused by this approximation are greater than in the semi-infinite case. Therefore, it would be advantageous to have a solution of the transport equation for a two-layered medium fast enough to be used for determination of the optical properties."

As described above, existing methods for imaging of tissue are inadequate because they do not provide us with the information we need to obtain, namely the three-dimensional spatial variation of the optical properties of said tissue, including the absorption coefficient, the scattering coefficient, and the asymmetry factor.

BRIEF DESCRIPTION OF THE SEVERAL VIEWS OF THE DRAWING(S)

FIG. 1 shows a schematic diagram of a multi-layered tissue.

Figure 2:
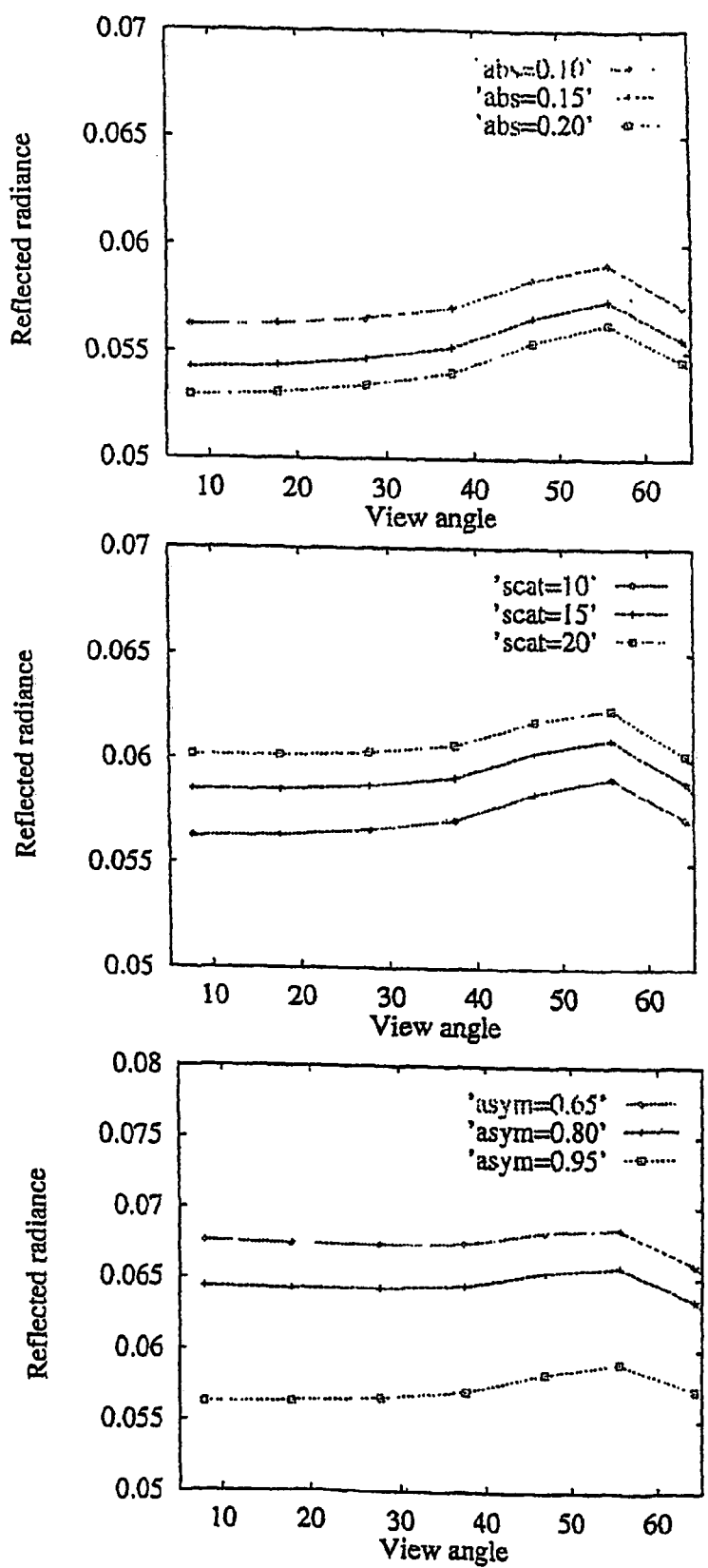

FIG. 2 shows simulations of reflected radiances for a 3-layer tissue model with an abnormal ("malignant") middle layer, and normal ("healthy") upper and bottom layers. The absorption and scattering coefficients for the "healthy" upper and bottom layers are taken to be $\alpha_{17}=\alpha_3=0.1$ mm$^{-1}$ and $\sigma_1=\sigma_3$ 10.0 mm$^{-1}$, while the asymmetry factor is fixed at $g_1=g_3$ 0.95. Upper left panel: The scattering coefficient of the middle layer is fixed at $\sigma_2=10.0$ mm$^{-1}$ and the asymmetry factor is $g_2=0.95$ (the same as for the "healthy" upper and bottom layers), but the absorption coefficient is allowed to vary. Upper curve: $\alpha_2=10.0$ mm$^{-1}$ ("healthy" value); Middle curve: $\alpha_2=0.15$ mm$^{-1}$ ("malignant" value); Lower curve: $\alpha_2=0.20$ mm$^{-1}$ ("malignant" value). Upper right panel: The absorption coefficient of the middle layer is $\alpha_2=0.1$ mm$^{-1}$ and the asymmetry factor is $g_2=0.95$ (the same as for the "healthy" upper and bottom layers), but the scattering coefficient is allowed to vary. Lower curve: $\alpha_2=0.10$ mm$^{-1}$ ("healthy" value); Middle curve: $\alpha_2=15$ mm$^{-1}$ ("malignant" value); Upper curve: $\sigma_2=20$ mm$^{-1}$ ("malignant" value). Lower panel: The absorption coefficient of the middle layer is $\alpha_2=0.1$ mm$^{-1}$ and the scattering coefficient is $\sigma_2=10.00$ mm$^{-1}$ (the same as for the "healthy" upper and bottom layers), but the asymmetry factor is allowed to vary. Lower curve: $g_2=0.95$ ("healthy" value); Middle curve: $g_2=0.80$ mm$^{-1}$ ("malignant" value); Upper curve: $g_2=0.65$ mm$^{-1}$ ("malignant" value).

Figure 3:
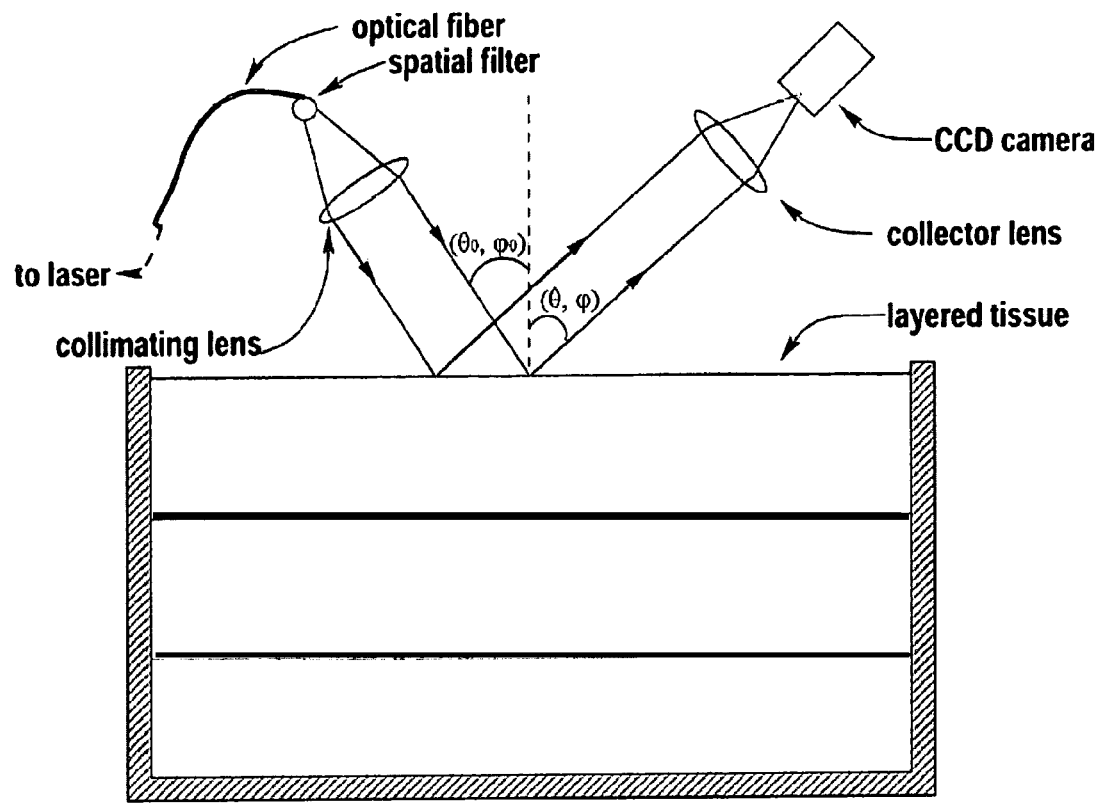

FIG. 3 shows a schematic diagram of the experimental setup.

BRIEF DESCRIPTION OF THE INVENTION

Our novel concept for characterizing biological tissues and retrieving their optical properties is based on a comprehensive radiative transfer model together with multi-angle illumination and viewing at several wavelengths. Thus we propose to illuminate the tissue successively from several different directions by an extended continuous-wave collimated beam. For each illumination direction we will measure the backscattered light successively in different viewing directions through directional scanning with a CCD camera.

The equipment required for these measurements consists of standard optical components and a CCD camera with suitable resolution and sensitivity. Neither temporal modulation of the illuminating beam to create a photon density wave nor fast electronics to do time gating will be required.

The multi-angle, multi-wavelength approach described above is very important in order to make the solution of the inverse problem unique. When using only one wavelength, one illumination direction, and one viewing direction, there may be many different combinations of optical properties of the various layers that give essentially the same backscattered light. To avoid this problem we constrain our solution of the inverse problem by forcing it to be consistent with many different sets of scattering data acquired from several different combinations of wavelengths as well as illumination and viewing directions. The solution of the inverse problem contains two main ingredients, which are described below.

One essential ingredient in our approach to the solution of the inverse problem is the creation of a synthetic database of simulated measurements. This is accomplished as follows. (1) For a given measurement configuration, we use rigorous forward modelling for the coupled air/tissue system to compute the field that would be measured for a given tissue configuration. Here the term "measurement configuration" means a particular combination of illuminating wavelength, illumination direction, and viewing direction, and the term "tissue configuration" means a particular combination of optical parameters in the various layers of the tissue. (2) We repeat the computations in (1) for a number of different tissue configurations so as to obtain look-up tables or a partial synthetic database of simulated measurements associated with the given measurement configuration. (3) We repeat the computations in (1) and (2) for many different measurement configurations in order to create a complete set of look-up tables or a complete synthetic database of simulated measurements that covers all desired combinations of measurement configurations and tissue configurations. The rigorous forward modelling for the coupled air/tissue system is described below under "Rigorous forward modelling".

The second essential ingredient of our inversion approach consists in comparing measured data for many different combinations of measurement configurations with simulated data contained in our synthetic database in order to determine that particular tissue configuration which provides best agreement between measured and synthetic data. To accomplish this in a cost-effective manner we employ the method of "global optimization" that is described below under "Inverse modelling to obtain tissue configuration".

To explain the novel concept of the present invention, we will start by considering a stratified multi-layered turbid medium. Thus we will assume that the tissue consists of plane parallel layers, each having different optical properties. To be specific we will first consider a tissue consisting of three layers, and each layer will be described by its optical properties, i.e. its i) absorption and scattering coefficients $\alpha$ and $\sigma$ ii) asymmetry parameter g, and iii) thickness z.

Note that the absorption and scattering coefficients and the asymmetry parameter are wavelength-dependent.

We employ the discrete-ordinate method (to be described below) to solve the radiative transfer equation pertaining to a slab of biological tissue that is stratified into a number of layers (FIG. 1). The radiative transfer equation provides a rigorous description of the transport of light in an absorbing and multiple scattering material, such as tissue. However, the change of the refractive index between the air and the tissue affects both the reflected field and the field inside the tissue significantly. Therefore, one must take the reflection and refraction of the incident light at the air/tissue interface into account to obtain a rigorous solution for the coupled air/tissue system (Z. Jin and K. Stamnes, Radiative transfer in non-uniformly refracting layered media, Appl. Opt. 33, 431-442, 1994; G. E Thomas and K. Stamnes, Radiative Transfer in the Atmosphere and Ocean, Cambridge University Press, 1999, section 6.6; A. R. Degheidy and M. S. Abdel Krim, Effects of Fresnel and diffuse reflectivities on light transport in a half-space medium, J. quant. Spectrosc. Radat. Transfer, 61, 751-757, 1999).

The assumption of a stratified tissue implies that the optical properties depend only on the depth. Radiative transfer in this stratified coupled air/tissue system can be described by the Radiative Transfer Equation (RTE), given as the first equation in section 6.6.1 in G. E. Thomas and K. Stamnes, Radiative Transfer in the Atmosphere and Ocean, Cambridge University Press, 1999 as follows:

$$u \frac{dI(\tau, u, \phi)}{d\tau} = I(\tau, u, \phi) - \frac{a(\tau)}{4\pi} \int_0^{2\pi} d\phi' \int_{-1}^{1} du' p(\tau, u', \phi'; u, \phi) I(\tau, u', \phi') - S^*(\tau, u, \phi)$$

where $I(\tau, u, \phi)$ is the diffuse radiance, and $$S^*(\tau, u, \phi) = \frac{a(\tau) I_0}{4\pi} \frac{\mu_0}{\mu_t} \mathcal{T}_b(-\mu_0; m_{rel}) p(\tau, -\mu_t, \phi_0; u, \phi) e^{-\tau/\mu_t}.$$

Here $m_{rel}$ is the index of refraction in the tissue relative to air, $I_o$ is the incident beam irradiance, $T_b(-\mu_0; m_{rel}) \equiv T_b(-\mu_0, \phi_0; -\mu_t, \phi_0; m_{rel})$ is the beam transmittance through the interface, $\mu_0$ is the cosine of the incident beam angle, and $\mu_t$ is the cosine of the refracted beam angle in the tissue, related to $\mu_0$ by Snell's Law $$\mu_t = \mu_t(\mu_0, m_{rel}) = \sqrt{1-(1-\mu_0^2)/m_{rel}^2}$$

In this RTE u' is cosine of the polar angle prior to scattering, u is the cosine of the polar angle after scattering, φ' is the azimuth angle prior to scattering, φ is the azimuth angle after scattering, τ is the optical depth, $a(\tau)=\sigma(\tau)/[\sigma(\tau)+\alpha(\tau)]$ is the single-scattering albedo, $\alpha(\tau)$ is the absorption coefficient, $\sigma(\tau)$ is the scattering coefficient, and p(τ, u', φ', u, φ,) is the scattering phase function, which gives the probability of scattering from an incident direction (u',φ') into an new direction (u, φ). Note that the internal source S*(τ,u,φ) depends on the direction ($\theta_0$, $\phi_0$) of the incident light (see FIG. 1), the collimated beam intensity, and the refractive index in the tissue relative to that in air. A numerical code that solves the multiple scattering problem for such an air/tissue system is described in Z. Jin and K. Stamnes, Radiative transfer in non-uniformly refracting layered media, Appl. Opt. 33, 431-442, 1994, and in section 6.6.1 in G. E Thomas and K. Stamnes, Radiative Transfer in the Atmosphere and Ocean, Cambridge University Press, 1999. The solution is obtained by employing the so-called discrete-ordinate method, which amounts to replacing the integral on the right-hand side of the RTE by a sum. Thereby, the original RTE, which is an integro-differential equation, is replaced by a set of ordinary differential equations, which are solved using standard techniques of linear algebra. Thus, one obtains a fast and rigorous forward modelling scheme for the coupled air/tissue system. For details, see Z. Jin and K. Stamnes, Radiative transfer in non-uniformly refracting layered media, Appl. Opt. 33, 431-442, 1994.

Rigorous Forward Modelling

Based on the three-layer model described above we will solve the Radiative Transfer Equation (RTE) to obtain the backscattered light for various angles of illumination and viewing. In this endeavor we will use the solution of the RTE for a coupled air/tissue system as described above, where the change in the refractive index between the air and tissue is taken into account. This is very important in order to get a correct description of the backscattered light.

As explained in detail previously, these simulations are carried out for many different tissue configurations (i.e. combinations of the optical properties in the three layers) in order to create look-up tables (i.e. a synthetic database of simulated measurements) for the backscattered intensity for a variety of measurement configurations (i.e. combinations of wavelengths and illumination and viewing angles). Such look-up tables are essential in order to obtain a reasonably fast solution of the inverse problem. The third or bottom layer will be assumed to be so thick that no radiation is scattered back from its bottom surface. We noted above that the optical properties depend on wavelength. Thus, by systematically varying the optical properties within their expected ranges for the wavelength interval of interest, we automatically include their wavelength dependence.

In our forward simulations we assume that the tissue layers in FIG. 1 have thicknesses of $z_1$, $z_2$, and $z_3$, respectively. The refractive indices of the air and the tissue are taken to be $n_1$ and $n_2$, respectively, and the absorption and scattering coefficients of layers 1, 2, and 3 are denoted by $\alpha_1$, $\alpha_2$ and $\alpha_3$ and $\sigma_1$, $\sigma_2$ and $\sigma_3$, respectively. The asymmetry factors of layers 1, 2, and 3 are denoted by $g_1$, $g_2$, and $g_3$, respectively. As explained previously, the scattering phase function gives the probability that a photon that is incident in the direction (u', φ') is scattered into the direction (u, φ). One step in the solution of the RTE involves expanding the scattering phase function in a series of Legendre polynomials, and the asymmetry factor is the first expansion coefficient in this series. It has the values g=0 for isotropic scattering or scattering that is symmetric about the forward direction, g=−1 for complete backscattering, and g=1 for complete forward scattering. Lacking better information about the scattering phase function, we will use the synthetic Henyey-Greenstein scattering phase function to describe the angular light scattering pattern due to particles in the tissue. This scattering phase function is given in equation (6.49) in G. E Thomas and K. Stamnes, Radiative Transfer in the Atmosphere and Ocean, Cambridge University Press, 1999, and it depends only on one parameter, namely the asymmetry factor. To provide an example of the capability of the radiative transfer model when applied to the coupled air/tissue system we consider the following cases below:

(1) We keep the optical properties of the upper and lower layer fixed, while allowing those of the middle layer (i.e. the asymmetry factor $g_2$ and the absorption and scattering coefficients $\alpha_2$ and $\sigma_2$) to vary. This is a simple way of mimicking a "malignant" layer located between two healthy layers. Our goal is to show that the reflected radiances are sensitive to changes in the optical properties of the "malignant" middle layer when the optical properties of layers 1 and 3 are kept fixed. Thus, FIG. 2 shows that the reflected radiances are sensitive to changes in the absorption and scattering coefficients ($\alpha_2$ and $\sigma_2$) and the asymmetry factor ($g_2$) of layer 2. This illustrates that the measured reflected radiances carry information that can be used to retrieve the optical properties of this layer.

(2) When either the absorption or the scattering coefficient is large, the photon penetration depth is small. If the photon penetration depth becomes less than the thickness of layer 1, reflected radiances are no longer sensitive to changes in the optical properties of layer 2. Also, the transmitted radiance then becomes too small to be measured by conventional detection techniques. For a specified direction of illumination the photon penetration depth can easily be determined by increasing the upper layer thickness until the reflected intensity does not change. Knowledge of the photon penetration depth is important, because the reflected photons do not carry any information about the tissue located beneath that depth.

(3) FIG. 2 displays results only for light at normal incidence. By keeping the middle layer thickness so large that no photons are expected to reach the lowest layer, we can vary the optical properties of the two upper layers in a systematic fashion to create look-up tables for the reflected light. Entries in these look-up tables will depend on the optical properties of each of the two upper layers as well as on the direction of the incident light and the viewing angle of the detector. The look-up tables will be designed to allow for retrieval of the optical properties of the two upper layers, the photon penetration depth, and the thickness of the upper layer.

Inverse Modelling to Obtain Tissue Configuration

The solution of the inverse problem to retrieve tissue optical properties from measurements of reflected radiances, will be based on forward modelling combined with a suitable optimization method (see, e.g. O. Frette, J. J. Stamnes, and K. Stamnes, Optical remote sensing of waters with vertical structure, Appl, Opt. 40, 1478-1487 (2001)). Our radiative transfer model for the air/tissue system will be used for simultaneous retrieval of the tissue optical properties (the absorption and scattering coefficients, and the asymmetry factor) and the layer thickness using the method described by O. Frette, J. J. Stamnes, and K. Stamnes, Optical remote sensing of marine constituents in coastal water: A feasibility study, Appl. Opt. 37, 8318-8326, 1998. To retrieve the optical properties of the three layers we will use inverse modelling based on the look-up tables or synthetic database described above. Thus we will compare the measured backscattered data with simulated backscattered data from the look-up tables for a variety of combinations of optical parameters ($\alpha_j$, $\sigma_j$, $g_j$, and $z_j$; j=1, 2, 3) for three layers. In this comparison we will use a "global optimization" method such as simulated annealing to find that combination of optical properties which minimizes the difference between measured data and simulated measured data stored in the look-up tables (see, e.g. O. Frette, J. J. Stamnes, and K. Stamnes, Optical remote sensing of marine constituents in coastal water: A feasibility study, Appl. Opt. 37, 8318-8326, 1998). Here the term global optimization refers to an optimization method that is used to search for a global minimum in a cost-effective manner among several local minima. An example of such a global optimization method is simulated annealing, which is described in H. Press, S.A. Teukolski, W.T. Wetterlig, and B. P. Flannery, Numerical Recipes, Cambridge University Press, 1992. It is important to emphasize that what we can retrieve using inverse radiative transfer modelling are values for the optical parameters $\alpha_j$, $\sigma_j$, $g_j$, at different wavelengths and $z_j$ (j=1, 2, 3). This knowledge can be used to determine the physiological state of the tissue.

Testing of the Retrieval Algorithm Using Synthetic Data

First we will test the inverse modelling approach described above by using synthetic data generated from the forward model. Thus we will use synthetic data for a variety of configurations other than those included in the look-up table as input to the inverse-modelling algorithm. The retrieved optical parameters are those that yield the minimum difference between the synthetic radiances and the radiances retrieved from the look-up tables.

Testing of the Retrieval Algorithm Using Data From a Controlled Experiment

After having tested the retrieval algorithm thoroughly in the way just described, we will carry out a controlled experimental test. To that end we will use a three-layer suspension, and in each layer we will have particles with known optical properties of known concentrations. But the optical properties and concentrations will vary from one layer to the next.

Horizontal Imaging Using the Independent Column or Pixel Approach

The next step in the development of the novel concept of the present invention for imaging of a tissue is to investigate under what circumstances we can apply the one-dimensional approach described above to a tissue with variation in the horizontal direction parallel to the layer interfaces. The basic assumption that we will make is that each pixel in the image receives backscattered light only from the vertical column that lies directly underneath the corresponding area on the air/tissue interface. Using this assumption, we can apply the retrieval algorithm described above independently to each pixel in the image and thus provide information about the horizontal variation of the optical properties of different vertical columns, one for each pixel in the image. Thus within the range of validity of this independent-pixel approximation we can obtain a three-dimensional image of the optical properties of the tissue.

Testing of the Independent-Pixel Approach Using Synthetic Data

First we will test the independent-pixel approach described above by using synthetic data generated by use of forward modelling. Again the physical model will consist of three layers, but now there will be an abrupt change in its vertical physical and optical properties at a certain horizontal position. To generate synthetic data in this case we will use Monte Carlo simulations. In the retrieval we examine how close to the horizontal position of discontinuity we can place the area under investigation on the air/tissue interface, before the corresponding pixel in the image starts to deteriorate. In this manner a good estimate of the range of validity of the independent-pixel approach is obtained.

Testing of the Independent-Pixel Approach Using Data From a Controlled Experiment In a similar manner as described above for the testing of the one-dimensional retrieval algorithm, a controlled experimental test of the independent-pixel algorithm is conducted. A three-layer suspension is used, and in each layer we will have particles with known optical properties of known concentrations. But now we will arrange to have an abrupt change of the optical properties at a given horizontal position.

Three-Dimensional Imaging Beyond the Independent-Pixel Approximation

The experimental data acquired by the multi-angle illumination and viewing approach described above can also be applied to obtain an image that is not based on the independent-pixel approximation. Dependent upon the outcome of the testing of the independent-pixel approach, as described above, we will decide whether it is worthwhile to develop inverse modelling methods that are not based on this approximation.

Experimental Setup

FIG. 3 shows a sketch of the experimental arrangement in accordance with the present invention. A collimated laser beam is incident upon the air/tissue interface in the direction ($\theta_0$, $\phi_0$). The incident beam illuminates an extended area of the air/tissue interface, and some of the incident light is refracted through the air/tissue interface and penetrates into the tissue where it may be scattered or absorbed. A portion of the scattered light reaches the air/tissue interface and is refracted back through the interface in various directions. A CCD camera is directionally scanned to detect the light leaving the illuminated area of the interface in various directions ($\theta,\phi$). By directional scanning is meant to detect the light leaving the illuminated area of the interface from many different viewing directions. For each combination of illumination and viewing directions several different wavelengths will be used successively.

The Kr—Ar multi-line laser used in this experiment emits light at 5 wavelengths, i.e. at $\lambda$=458 nm, $\lambda$=488 nm, $\lambda$=514 nm, $\lambda$=530 nm, and $\lambda$=647 nm. The CCD camera used to detect the backscattered light has a high spatial resolution with 2048×2048 pixels and a dynamic range of 16 bits. In a preferred embodiment of the invention the CCD chip is cooled by a Peltzier element down to −32° C. in order to minimize the dark current noise. Both the laser and the detector are of high quality and are very well suited for the controlled experiments.

The scattering medium consists of three plane parallel layers with different optical properties. Each layer can be a liquid with a given density and absorption containing a suspension of scattering particles. Alternatively, each layer can be of a gelatine material with given absorption and scattering coefficients. The latter choice will be better for experiments over a prolonged period, since particles in a liquid suspension will tend to change their vertical position with time.

The feasibility of retrieving information about optical properties for an absorbing and scattering medium like tissue from experiments as described above, has recently been demonstrated for the coupled atmosphere/ocean system, see e.g. O. Frette, J. J. Stamnes, and K. Stamnes, Optical remote sensing of marine constituents in coastal water: A feasibility study, Appl. Opt. 37, 8318-8326, 1998; O. Frette, S. R. Erga, J. J. Stamnes, and K. Stamnes, Optical remote sensing of waters with vertical structure, Appl. Opt. 40, 1478-1487 (2001); Stamnes, K., W. Li, B. Yan, A. Barnard, W. S. Pegau and J. J. Stamnes, A new ocean color algorithm: Simultaneous retrieval of aerosol optical properties and chlorophyll concentrations, Appl. Opt., submitted. In this connection it is important to emphasize that the coupled atmosphere/ocean system is far more complicated than the air/tissue system. In the former case a simultaneous retrieval of optical properties in the atmosphere and ocean is required because 90% or more of the measured signal is due to absorption and scattering in the atmosphere. In the latter case it suffices to retrieve the optical properties of the tissue because the air does not significantly affect the measured signal.

The invention claimed is:

1. A method for determining optical properties of a multi-layered tissue, comprising the steps of:
   (a) illuminating an extended area of the multi-layered tissue by a continuous-wave collimated electromagnetic beam successively from a plurality of directions ($\theta_0, \phi_0$), the continuous-wave collimated electromagnetic beam providing for continuous illumination of the multi-layered tissue;
   (b) illuminating the extended area of the multi-layered tissue, for each of the plurality of illumination directions, at a plurality of different wavelengths ($\lambda$);
   (c) detecting reflected or scattered light leaving the illuminated area from a plurality of detection directions ($\theta, \phi$), for each of the plurality of illumination directions and each of the plurality of wavelengths for obtaining light measurement data in a one-dimensional schematic;
   (d) obtaining light measurement data in a one-dimensional schematic that corresponds to the detected reflected or scattered light obtained in the step of detecting;
   (e) populating a synthetic database with simulated measurements, the simulated measurements including data based on:
      (1) using a rigorous forward radiative transfer model for a coupled air/tissue system to compute simulated light measurement data for a particular tissue configuration and a particular measurement configuration, the particular tissue configuration including a particular combination of layer thicknesses and optical properties ($\alpha$, $\sigma$, and g) in the layers of the multi-layered tissue, and the particular measurement configuration including a particular combination of illumination wavelength, illumination direction, and detection direction,
      (2) repeating the computations in (1) for a plurality of different tissue configurations so as to obtain a portion of the synthetic database including simulated light measurement data associated with a particular measurement configuration, and
      (3) repeating the computations in (1) and (2) for a plurality of different measurement configurations to create the synthetic database of simulated light measurement data for a plurality of combinations of the particular measurement configurations and the particular tissue configurations; and
   (f) comparing the light measurement data of the multi-layered tissue with the data of the synthetic database via optimization to determine the optical properties of the multi-layered tissue.

2. The method according to claim 1, wherein an optimization method is used to determine that tissue configuration of a particular combination of the optical parameters ($\alpha$, $\sigma$, and g) in the various layers of the tissue, which minimizes differences between measured reflected or scattered light data and simulated reflected or scattered light data stored in the synthetic database.

3. The method according to claim 1, wherein the reflected or scattered light is detected by directional scanning with a CCD camera.

4. The method according to claim 1, wherein the multi-layered tissue is illuminated by polarized light, and that both the co-polarized and cross-polarized component of the scattered light are detected.

5. The method according to claim 1, wherein the multi-layered tissue is illuminated by light of various intensities.

6. An apparatus for determining the optical properties of a multi-layered tissue comprising:
   (a) a source producing a continuous-wave collimated electromagnetic beam adapted to illuminate a selected extended area of a multi-layered tissue successively from several directions, the continuous-wave collimated electromagnetic beam providing for continuous illumination of the multi-layered tissue;
   (b) wherein the selected extended area of the multi-layered tissue, for each illuminating direction, is illuminated by the source at a plurality of different wavelengths;
   (c) a detector, such as a CCD camera, adapted to detect light leaving the selected extended area in a plurality of viewing directions, for each illumination direction and wavelength and to generate corresponding light measurement data in a one-dimensional schematic; and
   (d) a synthetic database of simulated measurements, wherein the light measurement data measured by the detector are compared with simulated light measurement data in the synthetic database to determine the optical properties of the multi-layered tissue using an optimization method to determine that tissue configuration of a particular combination of optical properties ($\alpha$, $\sigma$, and g) in the various layers of the tissue, which minimizes differences between measured reflected or scattered light data and simulated reflected or scattered light data stored in the synthetic database.

7. A multi-layered tissue imaging system comprising:
   (a) a continuous-wave collimated beam source being configured to illuminate a selected extended area of a multi-layered tissue from a plurality of angular directions and at a plurality of wavelengths, the continuous-wave collimated electromagnetic beam providing for continuous illumination of the multi-layered tissue;
   (b) a scanning device configured to detect light leaving the illuminated area of the multi-layered tissue, to generate an image, and to generate corresponding light measurement data in a one-dimensional schematic; and
   (c) a synthetic database of simulated measurements associated with the multi-layered tissue, the synthetic database including simulated measurements derived from at least one tissue and measurement configuration, the at least one tissue configuration including optical parameters in the various layers of the tissue, and the at least one measurement configuration including an illumination wavelength, an illumination direction, and a detection direction, wherein the light measurement data in the image are compared with simulated data in the synthetic database to determine optical properties of the illuminated tissue, wherein the optical properties include light absorption coefficients, light scattering coefficients, and light scattering asymmetry factors.

8. A multi-layered tissue imaging system as recited in claim 7, wherein the imaging system is configured to diagnose and localize tumors in the tissue.

9. A multi-layered tissue imaging system as recited in claim 7, wherein the continuous-wave collimated beam source includes a laser.

10. A multi-layered tissue imaging system as recited in claim 7, wherein the continuous-wave collimated beam source includes a laser diode.

11. A multi-layered tissue imaging system as recited in claim 7, wherein the scanning device includes a CCD camera.

12. A multi-layered tissue imaging system as recited in claim 7, wherein the scanning device includes detectors.

13. A multi-layered tissue imaging system as recited in claim 7, wherein the continuous-wave collimated beam source includes a light emitting diode.

14. A multi-layered tissue imaging system as recited in claim 7, wherein a morphological and physiological state of the tissue is determined.

15. A method for determining optical properties of a multi-layered tissue, the method comprising the steps of:
(a) illuminating a selected extended area of the multi-layered tissue by a continuous-wave collimated electromagnetic beam successively from several directions ($\theta o$, $\Phi o$), the continuous-wave collimated electromagnetic beam providing for continuous illumination of the multi-layered tissue;
(b) illuminating the multi-layered tissue, for each of the several directions, at a multitude of different wavelengths ($\lambda$);
(c) detecting reflected and scattered light leaving the illuminated area at a multitude of different detecting directions ($\theta$, $\Phi$);
(d) using a rigorous radiative transfer model for the coupled air/tissue system to compute the reflected and scattered light for a plurality of the wavelengths ($\lambda$), a plurality of the illuminating directions ($\theta o$, $\Phi o$), and a plurality of the detecting directions ($\theta$, $\Phi$), for a plurality of multi-layered tissues in order to produce a synthetic database; and
(e) subjecting an uncharacterized multi-layered tissue to a similar step of illuminating as in steps (a) and (b), and detecting as in step (c) to produce detected light data and wherein the detected light data are compared to data in the synthetic database in order to provide a unique indication of the characteristics of the multi-layered tissue.

* * * * *